US00PP12540P2

(12) United States Plant Patent
Zerr

(10) Patent No.: US PP12,540 P2
(45) Date of Patent: Apr. 9, 2002

(54) POINSETTIA PLANT NAMED 'FISSON JINGLE'

(75) Inventor: Katharina Zerr, Höhr-Grenzhausen (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/099,775

(22) Filed: Jun. 19, 1998

(51) Int. Cl.[7] ..... A01H 5/00
(52) U.S. Cl. ..... Plt./303
(58) Field of Search ..... Plt./303, 306, 307

(56) References Cited

U.S. PATENT DOCUMENTS

PP4,860 P * 6/1982 Ecke, Jr. ..... Plt./303
PP7,308 P * 8/1990 Fruehwirth ..... Plt./303
PP8,771 P * 6/1994 Fruehwirth ..... Plt./303

OTHER PUBLICATIONS

GTITM UPOVROM Citation for 'Fisson Jingle' as per CA PBR 96–964; Oct. 15, 1996.*
GTITM UPOVROM Citation for 'Fisson Jingle' as per JP PBR 93381; Dec. 27, 1996.*
German Plant Breeder's Rights Application No. EUP 194, applied Oct. 30, 1996 (application withdrawn).
Japan Plant Breeder's Rights Application No. 993381, applied Dec. 27, 1997.
Pelfi Fischer 1997 Poinsettien Katalog featuring 'Sonora Jingle' p. 5; Germany.

* cited by examiner

*Primary Examiner*—Bruce R. Campell
*Assistant Examiner*—Kent L. Bell
(74) *Attorney, Agent, or Firm*—Foley & Lardner

(57) ABSTRACT

'Fisson Jingle' is characterized by bright-red colored bracts with relatively small and numerous light-pink spots; flat inflorescences with medium-sized bracts which are distinctly lobed with pointed tips; intense dark-green foliage which is distinctly lobed and a compact and bushy plant habit.

1 Drawing Sheet

BACKGROUND OF THE INVENTION

The present invention relates to a new and distinct cultivar of poinsettia plant known by the cultivar name 'Fisson Jingle', and botanically known as *Euphorbia pulcherrima.*

'Fisson Jingle' is a product of a mutation induction program carried out by the inventor, Katharina Zerr, in Hillscheid, Germany, in 1994.

The primary objective of the induction program was to expand the bract color ranges of 'Fisson', a cultivar claimed in U.S. Plant Pat. No. 9,365. 'Fisson' is characterized by its bright red bracts with pointed lobes, dark-green foliage and relatively compact habit.

The irradiation program comprised exposing rooted cuttings taken from plants of the cultivar to an X-ray source of 30 Gy dosage in Ahrensburg, Germany, under the supervision of the inventor.

The irradiated plants were grown out in a greenhouse in Hillscheid, Germany, and were asexually propagated by the inventor by taking cuttings. The plants resulting from these cuttings were screened for mutations as small flowering single-stem plants in the autumn and winter of 1994. One plant was selected and designated 182/1. Plants of 182/1 were grown out and one plant of 182/1 exhibited a mutation of interest. This mutation of interest was grown out and designated 182/2 for evaluation purposes. 182/2 was later named 'Fisson Jingle'.

'Fisson Jingle' originated as a branch mutation of a proprietary selection designated 182/1 (unpatented). 'Fisson Jingle' was asexually reproduced, by the inventor, through vegetative cuttings, specifically terminal shoot cuttings with 3–4 mature leaves, in Hillscheid, Germany in April 1996.

Horticultural examination starting in 1996 has confirmed that the combination of morphological characteristics disclosed for 'Fisson Jingle' are firmly fixed and retained through successive generations of asexual reproduction.

BRIEF DESCRIPTION OF THE INVENTION

The following traits have been repeatedly observed and are determined to be basic characteristics of 'Fisson Jingle' which in combination distinguish this Poinsettia as a new and distinct cultivar:

1. Bright-red colored bracts with relatively small and numerous light-pink spots; up to 10% of the spots are larger and cover a section of the leaf between the veins and midrib;

2. Flat inflorescence with medium-sized bracts which are distinctly lobed with pointed tips;

3. Intense dark-green foliage which is distinctly lobed;

4. Compact, bushy and very well-branched plant habit which makes the cultivar suitable for use as a pot plant;

5. Medium early-flowering response; and,

6. Good post production keeping quality.

'Fisson Jingle' has not been observed under all possible environmental conditions. The phenotype may vary significantly with variations in environment such as temperature, light intensity, and daylength without, however, any variance in genotype. The following observations, measurements and comparisons describe plants grown in Langley, British Columbia, Canada, under greenhouse conditions which approximate those generally used in commercial practice.

The new cultivar 'Fisson Jingle' differs from its parent 182/1 primarily in bract coloration.

Of the many commercial cultivars known to the inventor, the most similar in comparison to 'Fisson Jingle' are the cultivar 'Fisson' and the commercial cultivar '490 Jingle Bells' (U.S. Plant Pat. No. 8,771).

In comparison to the bright red colored cultivar 'Fisson', the new cultivar 'Fisson Jingle' has a similar main bract color but is covered with numerous pink spots. Additionally, 'Fisson Jingle' petioles do not have the intense red color of those from 'Fisson'. Likewise, the 'Fisson Jingle' petioles show a light red or green lines.

Other morphological characteristics of 'Fisson Jingle' are very similar to 'Fisson'.

In comparison to 'Freedom Jingle Bells', 'Fisson Jingle' has smaller bracts with a more smooth surface and distinct lobes, and its main bract color is a more intense red, while 'Freedom Jingle Bells' tends to fading, especially when grown at high temperature.

The flower response of 'Fisson Jingle' is somewhat later, while development and retention of the cyathia is better than '490 Jingle Bells'. Furthermore, the plant habit of 'Fisson Jingle' is usually more compact than '490 Jingle Bells'.

BRIEF DESCRIPTION OF THE DRAWING

The accompanying color photographic sheet shows typical inflorescence and foliage of 'Fisson Jingle', with colors being as true as possible with illustrations of this type. The photograph shows a typical mature potted plant.

DETAILED BOTANICAL DESCRIPTION

The plants described were grown in a greenhouse in Langley, British Columbia, Canada, in autumn 1996. Rooted cuttings were planted into 15 cm pots on August 12, and were pinched on August 30, leaving 8 nodes. The plants described were about 16 weeks old from the date of planting. The minimum temperature was 23° C. in August to October, and 20° C. from October 10 to mid-November. The plants initiated flowers under natural short-day conditions in autumn. Observations and measurements were mainly taken at the beginning of flowering. In the following description, color references are made to The Royal Horticultural Society Colour Chart. The color values were determined indoors in a north light.

Classification:

*Botanical.*—*Euphorbia pulcherrima.*

*Commercial.*—Poinsettia, cv. 'Fisson Jingle'.

Parentage: Naturally occurring branch mutation of proprietary selection 182/1 (unpatented).

Plant description:

*Form.*—Shrub, self-branching.

*Growth habit.*—Moderately compact and freely branching, pinched plants are bushy and round in shape; height (above soil line) is approx. 39.7 cm; average number of branches is approximately 6.7.

*Rooting.*—Medium, about 20 days.

*Blooming habit.*—Begins flowering under natural short-day conditions in autumn; botanically (cyathia open), in early December; commercially (bracts colored and marketable), around December 1; flowering response time is about 9.5 weeks.

*Foliage.*—Shape: Basal part of the leaf roughly triangular with acute base, strong pointed lobes, and with acuminate tip; smaller leaves without lobes are broad elliptically shaped. Size: Leaf blade length is 13.8 cm, leaf blade width is 11.5 cm; Petiole is about 7.0 cm long. Color: Generally dark green.

*Mature foliage.*—Upper surface, about RHS 147A; under surface 147B.

*New foliage.*—Upper surface is RHS 137A; under surface is RHS 137C. Leaf Petiole: Mainly brownish red, RHS 180A, with narrow green lines (for comparison 'Fisson' is RHS 60A and uniform). Texture: Upper surface smooth and flat. Margin: Entire.

Flowering description:

*Inflorescence.*—Flat, with the bracts borne horizontally and tips slightly overhanging; at the beginning of flowering there may be small gaps within the colored part of the inflorescence due to the narrow bases of the bracts; good keeping quality.

*Diameter.*—About 26 cm.

*Average number of inflorescence.*—6.5; approximately 85% of the branches develop a complete inflorescence.

*Bracts, shape.*—Larger bracts are roughly triangular, with wedge-shaped bases and distinctly lobed with pointed tips; the smaller, upper bracts are broad elliptically shaped and usually without lobes.

*Surface.*—Flat or slightly folded, occasionally somewhat rugose.

*Size.*—Largest bract, blade, length is 12.5 cm; largest bract, blade width is 10.6 cm (including lobes); largest bract, petiole is 1.5–2.0 cm.

*Color.*—Mainly bright-red with small pink, mainly oval-shaped spots; upper surface, main color is from RHS 46B to 46C and spots are RHS 51B or 51C (for comparison, '490 Jingle Bells' main color is from RHS 46C to 46D); lower surface is about from RHS 46C to 46D, spots are from RHS 51C to 51D.

*Number.*—Approximately 5–6 true bracts at the beginning of flowering with two completely colored transient bracts.

*Post-production longevity.*—Approximately 30 days in winter conditions in Europe, no change of the bract color; the retention of foliage and bracts is relatively good due to the chlorophyll stability of the dark-green foliage.

*Petiole.*—Dark red near RHS 53B, occasionally narrow green lines.

*Cyathias.*—Borne: In a narrow cluster, few, about 10–14, approximately 20 mm in diameter; retention is medium. Color: Light to medium green, top red. Nectar Cups: Small to medium sized, golden yellow, and no anthocyanin.

Reproductive organs:

*Stamens.*—Filaments are red.

*Pollen.*—Yellow and plentiful.

*Pistils.*—Style and stigma are red; 6-lobed stigma.

*Ovaries.*—Light to medium green; triangular, 3-celled; 3 ovules.

*Resistance/susceptibility to disease.*—No observations to date.

I claim:

1. A new and distinct poinsettia plant named 'Fisson Jingle', as illustrated and described.

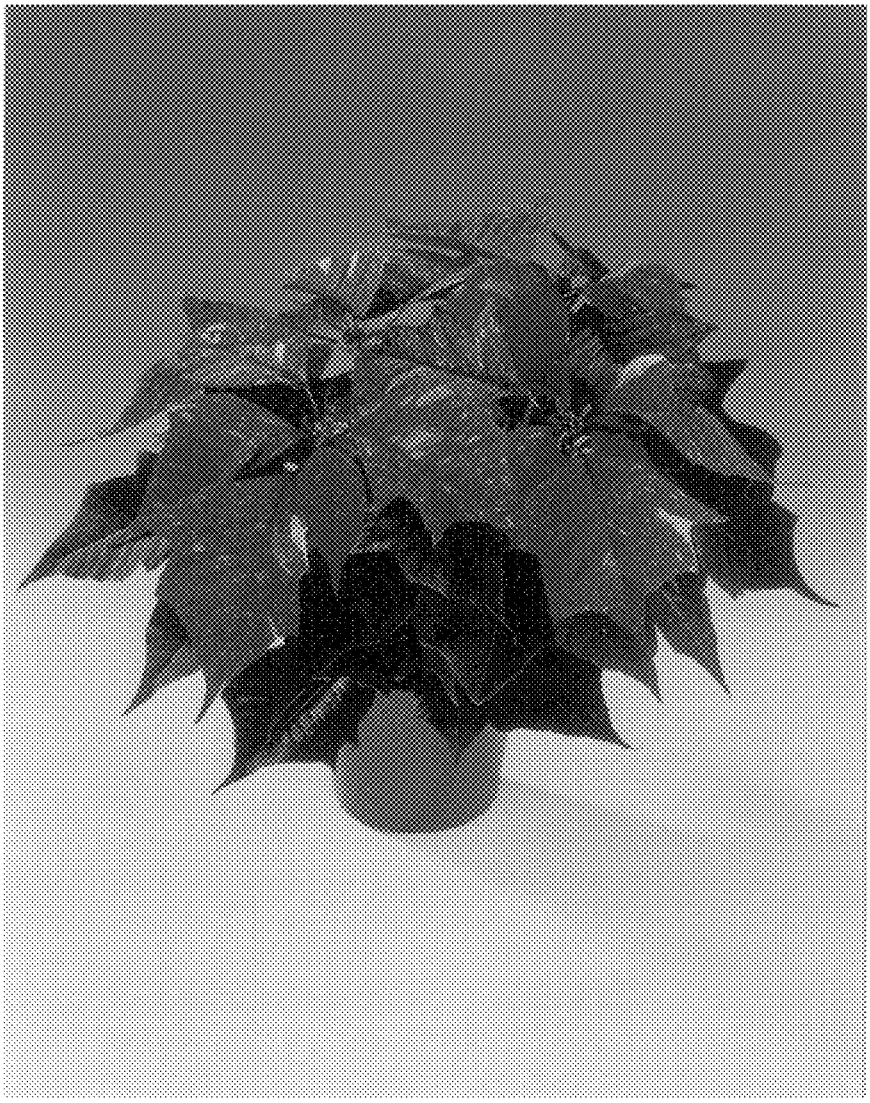

* * * * *